United States Patent [19]

Short

[11] Patent Number: 5,383,846
[45] Date of Patent: Jan. 24, 1995

[54] FINGER MOUNTED MOISTURE ABSORBING DEVICE

[76] Inventor: Thomas C. Short, 7440 La Vista Dr. - Apt. 253, Dallas, Tex. 75214-4283

[21] Appl. No.: 840,011

[22] Filed: Feb. 24, 1992

[51] Int. Cl.$^6$ .............................................. A61F 13/00
[52] U.S. Cl. .................................... 602/59; 602/61
[58] Field of Search ................. 602/22, 44, 56, 63, 602/64, 21, 20, 59, 60, 61; 2/21; 128/880

[56] References Cited

U.S. PATENT DOCUMENTS

| | | | |
|---|---|---|---|
| 692,503 | 2/1902 | Bottomley | 602/63 |
| 1,231,194 | 6/1917 | Prince | 2/21 |
| 2,461,872 | 2/1949 | Beatty | 2/21 |
| 2,461,970 | 2/1949 | Finegen | 2/21 |
| 2,740,121 | 4/1956 | Seidel | 2/21 |
| 2,847,005 | 8/1958 | Bourne | 2/21 |
| 3,306,288 | 2/1967 | Rosenfield | 602/63 |
| 3,513,842 | 5/1970 | Keenan | 602/63 |
| 4,126,130 | 11/1978 | Cowden | 602/22 |
| 4,733,410 | 3/1988 | Glotkin | 2/21 |
| 5,095,897 | 3/1992 | Clark | 2/21 |

Primary Examiner—Michael A. Brown
Attorney, Agent, or Firm—Jones, Day, Reavis & Pogue

[57] ABSTRACT

A finger-mounted moisture-absorbing device for use by individuals undergoing aerobic exercise such as long-distance running for wiping perspiration from the eyes. It is generally tubular in shape and formed preferably of a synthetic chamois sold under the trade name PLAS CHAMOIS. The tubular shape is formed from a generally rectangular sheet of moisture-absorbing material that is rolled to form substantially a circle with opposed outer ends of the rectangle in adjacent relationship. The opposed outer ends are either sewn together or are attached by an elastic strip or strips to allow the device to fit various sized fingers. The tubular member maybe enclosed at one end and opened at the other for insertion of a finger so as to enclose the entire finger.

7 Claims, 1 Drawing Sheet

FINGER MOUNTED MOISTURE ABSORBING DEVICE

BACKGROUND OF THE INVENTION

It is well known in the athletic field that those who do aerobic exercises, long distance running, power lifting and the like wherein the body perspires extensively utilize headbands and wristbands to keep the perspiration out of the eyes and from dripping down the hands, respectively.

In many instances, however, such as in long distance running, the moisture soaks the headband or seeps under the headband and gets in the eyes. Obviously the perspiration serves as an irritant for the eyes and it is difficult for the runner to remove the perspiration from around the eyes either because the headband or wristband are already soaked or it is difficult to try to use the wristband to get into the sockets of the eyes to remove any perspiration. Further, when the headband or wristbands are soaked, simply wringing them out does not sufficiently remove the moisture so that they can be used again to remove perspiration from the eye sockets.

The present invention overcomes the disadvantages of the prior art by providing a finger mounted moisture absorbing device that can be easily used to remove the perspiration from small areas such as the eyes. Further, the material of which the moisture absorbing device is preferably formed is sold under the trade name PLAS CHAMOIS and is made by Kanebo, Ltd. in Japan. This material is a synthetic chamois which soaks up moisture instantly, holds more moisture than a real chamois, wrings out more easily than towels or a natural chamois, is very soft and will not hurt delicate finishes or the delicate tissues around the eyes and can be machine washed with regular laundry. Thus, if the finger worn moisture absorbing device becomes soaked, it is a simple process for the user, without stopping his exercise, to remove the finger band, squeeze it gently to squeeze all the moisture out and replace it on the finger. It is formed of a generally rectangular sheet of moisture absorbing material, rolled to form substantially a circle with opposed outer ends of the rectangle in adjacent relationship. The adjacent ends are either sewn together to form a tubular member for mounting on a finger such that the device can be used as a moisture removing device. An alternate material that can be used is terry cloth, but it does not allow moisture to be removed easily once it is soaked. Of course, a real chamois could be used but it does not hold as much moisture as the synthetic chamois.

In one embodiment, the tubular member is enclosed at one end and opened at the other for insertion of a finger and thus resembles the finger of a glove. In another embodiment, the opposed outer ends of the rectangle are sewn together to form a seam.

In still another embodiment, an elastic strip is sewn between the opposed outer ends of the rectangular sheet of material to allow the tubular member to be enlarged to fit various sized fingers by stretching the elastic. In still another embodiment, the opposed outer ends of the rectangular sheet of material are attached together by spaced elastic strips sewn between the opposed outer ends to allow the tubular member to be enlarged to fit various sized fingers by stretching the elastic strips.

Thus, it is an object to the present invention to provide a finger-mounted moisture-absorbing device particularly useful for long-distance runners that is formed of a generally rectangular sheet of moisture absorbing material that is rolled to form substantially a circle with the opposed outer ends of the rectangle in adjacent relationship. Attachment means holds the opposed outer ends to form a tubular member for mounting on a finger such that the device can be used as a moisture removing device through moisture absorption by the material.

It is another object of the present invention to provide a finger-mounted moisture-absorbing device which is tubular in shape and which is formed of a synthetic material sold under the trade name PLAS CHAMOIS.

It is yet another object of the present invention to provide a finger-mounted moisture-absorbing device in the shape of a tubular member that is enclosed at one end and opened at the other for insertion of a finger.

It is still another object of the present invention to provide a finger-mounted moisture-absorbing device wherein the outer ends of the generally rectangular sheet of moisture-absorbing material are sewn together to form a seam.

It is yet another object of the present invention to provide a finger-mounted moisture-absorbing device formed of a generally rectangular sheet of moisture-absorbing material rolled to form substantially a circle and in which an elastic strip is sewn between the opposed outer ends of the rectangular sheet to allow the tubular member to be enlarged to fit various sized fingers.

It is also an object of the present invention to provide a finger-mounted moisture-absorbing device formed of a generally rectangular sheet of moisture-absorbing material that is rolled into a tubular form wherein spaced elastic strips are sewn between the opposed outer ends of the rectangular sheet to allow the tubular member to be enlarged to fit various sized fingers.

SUMMARY OF THE INVENTION

Thus, the present invention relates to a finger-mounted moisture-absorbing device comprising a generally rectangular sheet of moisture-absorbing material rolled to form substantially a circle with opposed outer ends of the rectangle in adjacent relationship and attachment means holding the opposed outer ends so as to form a tubular member for mounting on a finger such that the device can be used as a moisture-removing device through moisture absorption by the material.

BRIEF DESCRIPTION OF THE DRAWINGS

These and other objects of the present invention will be more fully understood in conjunction with the accompanying detailed description and the drawings in which like numerals represent like elements and in which.

DETAILED DESCRIPTION OF THE DRAWINGS

Figure 1:
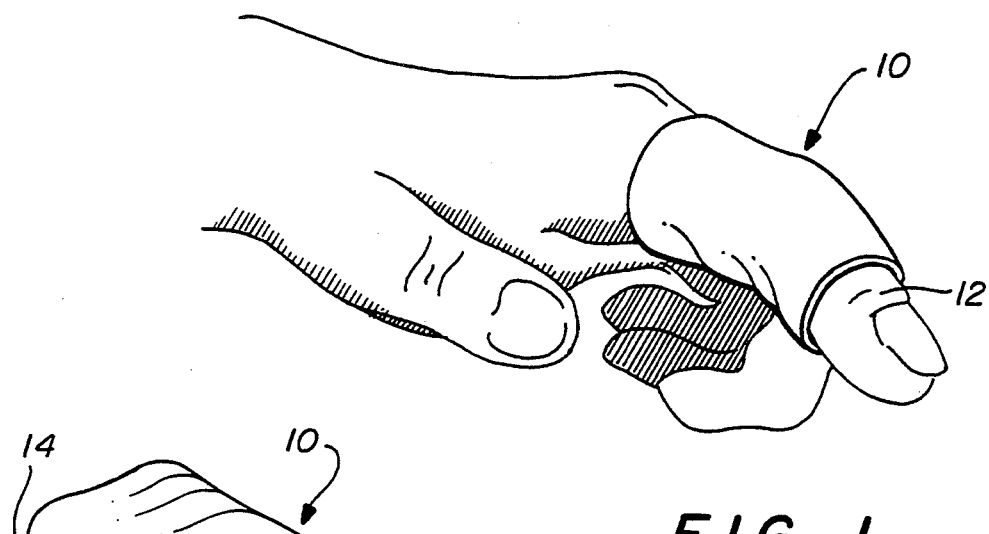
FIG. 1 is a perspective view of a hand with a finger having the novel tubular shaped moisture-absorbing device mounted thereon.

FIG. 1 is a perspective view of the hand of a person who may be engaged in an exercise during which he desires to wipe or remove perspiration from his eyes. In FIG. 1, a finger-mounted moisture-absorbing device 10 is shown mounted on the finger 12. The device 10 may be formed of any moisture-absorbing material; however, the preferred material is a synthetic chamois sold under the name PLAS CHAMOIS by a company entitled Kanebo, Ltd. of Japan. Natural chamois would also function well but it does not hold as much moisture as the synthetic chamois.

Figure 2:
FIG. 2 is a perspective view of one embodiment of the present invention illustrating a generally circular tubular member that has been formed of a generally rectangular sheet of moisture-absorbing material rolled to form substantially a circle and the opposed outer ends of the rectangle being sewn together to form a seam to shape the tubular member for insertion on the finger.

FIG. 2 is a perspective view of one embodiment of the present invention wherein the moisture absorbing device 10 can be seen to be a generally rectangular sheet of material that has been rolled to form substantially a circle with opposed outer ends 16 and 18 in adjacent relationship and being sewn together to form the tubular member for insertion of a finger as illustrated in FIG. 1. This version will fit generally one size finger.

Figure 3:
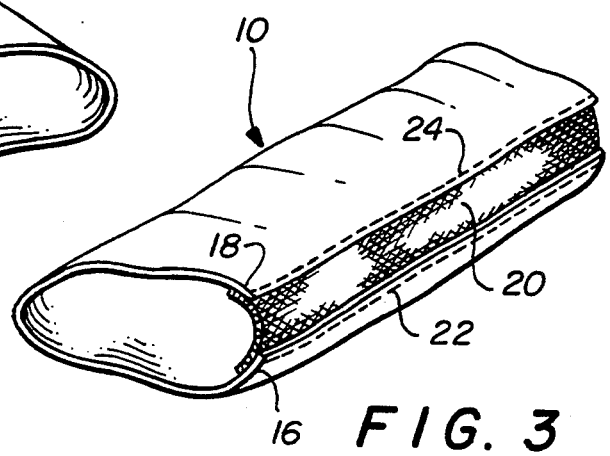
FIG. 3 is another embodiment of the present invention in which the finger-mounted moisture-absorbing device is formed of a generally rectangular sheet of moisture-absorbing material that has been rolled to substantially a circle and with the outer opposed ends of the rectangle held together by an elastic strip sewn therebetween to allow the tubular member to be enlarged to fit various size fingers.

In order to make the device available for use on various sized fingers, FIG. 3 illustrates a version in which the device 10 has the outer ends 16 and 18 coupled by an elastic device 20, which is in the form of a strip that has been sewn to the outer ends 16 and 18 by thread as indicated by lines 22 and 24. With this device, the elastic can stretch and allow the device 10 to fit various sized fingers.

Figure 4:
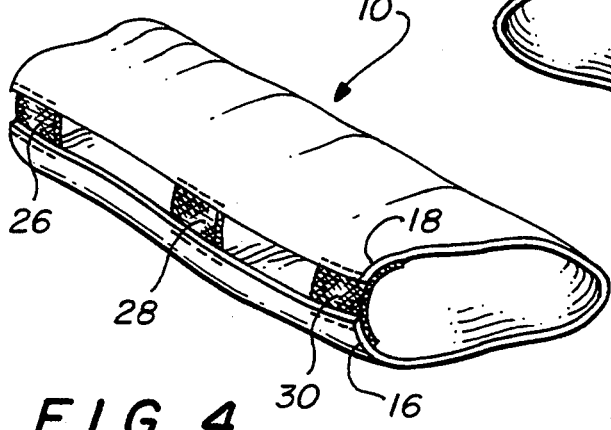
FIG. 4 is still another embodiment of the present invention in which the outer ends of the rectangular sheet of moisture-absorbing material have been attached together with spaced elastic strips sewn between the opposed outer ends to allow the tubular member to be enlarged to fit various size fingers.

FIG. 4 is an alternate version in which the device 10 has the outer edges 16 and 18 joined together by elastic strips 26, 28 and 30. Again each of these strips is sewn to the outer edges 16 and 18. Again, the device becomes variable in size because of the elastic strips 26, 28 and 30 and can therefore fit various sized fingers.

Figure 5:
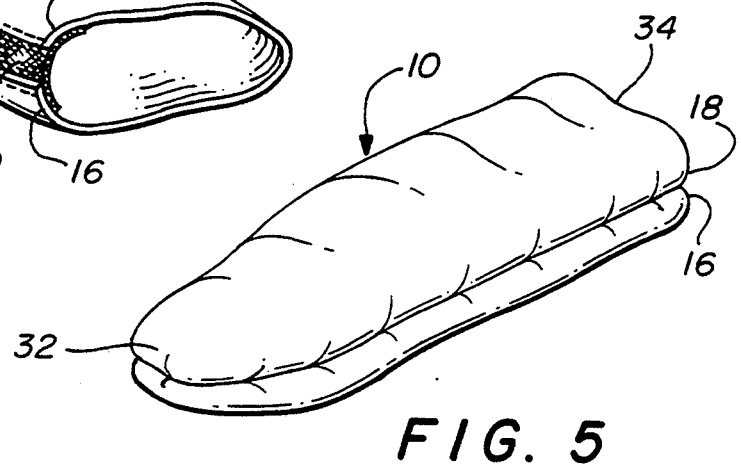
FIG. 5 is another embodiment of the present invention in which the tubular member is enclosed at one end and open at the other end for an insertion of a finger and for covering the entire finger.

In the embodiment illustrated in FIG. 5, the tubular member 10 is enclosed at one end as indicated by the numeral 32 and is opened at the other end as indicated by the numeral 34, thus the outer ends 16 and 18 of the tubular member 10 may be joined in any of the manners illustrated in the preceding FIGS. 2, 3, and 4, but is shown in FIG. 5 as being sewn together. This embodiment forms a complete cover for the finger from the outer tip of the finger to the point of attachment of the finger on the hand.

In use, the individual, such as the long-distance runner, utilizes the device 10 to remove perspiration or sweat from his eyes. When the device 10 becomes soaked, he simply gently squeezes the chamois 10 either while on his finger or removed therefrom to cause the liquid held therein to be removed from the chamois and it can be used again. The runner can squeeze the water or moisture out of the chamois 10 as it accumulates and thus continue to use the device.

Thus, there has been disclosed a novel finger-mounted moisture-absorbing device which can be used, in particular, for removing moisture from the eye that accumulates during aerobic exercise such as long-distance running. The device is made of a synthetic chamois in the preferred embodiment, although other moisture-absorbing materials could be used. The device is formed so as to cover the entire finger or a portion of the finger. Further the device is constructed in alternate embodiments to allow it to be adjustable in size to fit different sized fingers.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

I claim:

1. A finger-mounted moisture-absorbing device to enable an athlete to remove moisture from small areas such as the eyes, the device comprising:

a generally rectangular sheet of moisture-absorbing material rolled to form substantially a tube with opposed outer ends of the rectangle in adjacent relationship; and attachment means holding the opposed outer ends to form a tubular member for mounting on a finger such that the device can be used as a moisture-removing device through moisture absorption by the material and the moisture squeezed from the material without removal from the finger.

2. A finger-mounted moisture-absorbing device as in claim 1 wherein the moisture absorbing material is a synthetic chamois sold under the trademark PLAS CHAMOIS.

3. A finger-mounted moisture-absorbing device as in claim 1 wherein the moisture-absorbing material is terry cloth.

4. A finger-mounted moisture-absorbing device as in claim 1 wherein the tubular member is enclosed at one end and opened at the other for insertion of a finger so as to enclose the entire finger.

5. A finger-mounted moisture absorbing device as in claim 1 wherein the attachment means is a seam formed by sewing the opposed outer ends together.

6. A finger-mounted moisture-absorbing device as in claim 1 wherein the attachment means is an elastic strip sewn between the opposed outer ends of the rectangular sheet to allow the tubular member to be enlarged to fit various sized fingers.

7. A finger-mounted moisture-absorbing device, as in claim 1 wherein the attachment means comprises spaced elastic strips sewn between the opposed outer ends of the rectangular sheet to allow the tubular member to be enlarged to fit various sized fingers.

* * * * *